(12) United States Patent
Tsunoda

(10) Patent No.: US 7,454,948 B2
(45) Date of Patent: Nov. 25, 2008

(54) METHOD OF MEASURING COEFFICIENT OF DYNAMIC FRICTION BETWEEN GOLF BALL AND COLLISIONAL PLATE

(75) Inventor: Masaya Tsunoda, Kobe (JP)

(73) Assignee: SRI Sports Ltd., Kobe-shi (JP)

( * ) Notice: Subject to any disclaimer, the term of this patent is extended or adjusted under 35 U.S.C. 154(b) by 71 days.

(21) Appl. No.: 11/434,231

(22) Filed: May 16, 2006

(65) Prior Publication Data

US 2006/0272389 A1    Dec. 7, 2006

(30) Foreign Application Priority Data

Jun. 7, 2005    (JP)    ............................. 2005-167111

(51) Int. Cl.
*G01N 19/02* (2006.01)

(52) U.S. Cl. ........................... 73/9; 73/11.01; 73/11.04; 73/12.01; 73/12.02; 73/12.04

(58) Field of Classification Search ........................ 73/9, 73/11.01, 11.04, 12.01, 12.02, 12.04, 12.05
See application file for complete search history.

(56) References Cited

U.S. PATENT DOCUMENTS

| | | | |
|---|---|---|---|
| 6,354,966 B1 * | 3/2002 | Takemura et al. ............ | 473/374 |
| 6,367,800 B1 * | 4/2002 | Sheck et al. ................ | 273/372 |
| 6,497,625 B2 * | 12/2002 | Newby ........................ | 473/163 |
| 6,645,089 B2 * | 11/2003 | Tsunoda et al. .............. | 473/371 |
| 6,849,000 B2 * | 2/2005 | Chen ........................... | 473/161 |
| 6,942,579 B2 * | 9/2005 | Chen ........................... | 473/161 |
| 7,150,178 B2 * | 12/2006 | Bissonnette et al. ......... | 73/12.01 |
| 2002/0019268 A1 | 2/2002 | Tunoda et al. | |

FOREIGN PATENT DOCUMENTS

JP    2004-675 A    1/2004

\* cited by examiner

*Primary Examiner*—Edward Lefkowitz
*Assistant Examiner*—Freddie Kirkland, III
(74) *Attorney, Agent, or Firm*—Birch, Stewart, Kolasch & Birch, LLP

(57) ABSTRACT

By bringing a golf ball into collision with a collisional plate and measuring a coefficient of dynamic friction at this collision, contact force at the time of collision between an actual golf club and the golf ball is analyzed and spin rate of the golf ball is estimated. This invention provides a method for measuring a coefficient of dynamic friction between a golf ball and a collisional plate when the golf ball collides with the collisional plate disposed aslant at a predetermined angle with respect to a flying direction of the golf ball. The method includes concurrently obtaining a time function Fn(t) of contact force in the direction perpendicular to the collisional plate, and a time function Ft(t) of contact force in the direction parallel with the collisional plate; and determining as a coefficient of dynamic friction, a maximum value of a time function M(t) of ratio between Fn(t) and Ft(t) represented by M(t)=Ft(t)/Fn(t).

11 Claims, 3 Drawing Sheets

METHOD OF MEASURING COEFFICIENT OF DYNAMIC FRICTION BETWEEN GOLF BALL AND COLLISIONAL PLATE

This nonprovisional application is based on Japanese Patent Application No. 2005-167111 filed with the Japan Patent Office on Jun. 7, 2005, the entire contents of which are hereby incorporated by reference.

BACKGROUND OF THE INVENTION

1. Field of the Invention

The present invention relates to a method of measuring a coefficient of dynamic friction between a golf ball and a collisional plate when the golf ball collides with the collisional plate. Analysis of such measurement allows for prediction of a coefficient of dynamic friction at the time of hitting of a golf ball by an actual golf club and can facilitate adjustment of a spin rate of the golf ball.

2. Description of the Background Art

Spin rate of a golf ball is an important characteristic that controls flying distance performance and controllability. A golf ball having high spin rate is able to rapidly stop on the green due to back spin, and is controllable such that its flying path is a draw or a fade by applying side spin to a golf ball. For this reason, golf balls of high spin rate are favored by professional golfers and low-handicapped golfers.

Contrarily, golf balls having low spin rate are inferior in controllability due to their small back spin, however, they are superior in that they can achieve large flying distances. Therefore, they are frequently used by high-handicapped golfers.

Conventionally, spin rate is adjusted by making adjustments on various factors such as rigidity of the entire golf ball, its distribution, degree of rigidity of outermost layer, thickness of outermost layer, distribution of specific gravity of the entire golf ball and the like. For example, U.S. Publication No. 2002/0019268A1 proposes a multilayered golf ball which realizes a larger launch angle and a smaller back spin compared with conventional golf balls.

Meanwhile, in view of golf clubs, depth, width, size, shape, arranging interval of grooves, punch marks or the like formed in a face plane of a club head, as well as surface roughness of the face plane are adjusted. In one known approach, for example, surface roughness or the like of a face plane is changed depending on the club number so that the lower the number of club head, or the relatively smaller the loft angle, the smaller friction coefficient the face plane has, and that the higher the number of club head, the larger friction coefficient the face plane has (see Japanese Patent Laying-Open No. 2004-000675).

SUMMARY OF THE INVENTION

As described above, a friction coefficient that contributes to a spin rate of a golf ball depends on the combination of a type of golf ball and a surface structure of a golf club head. And, estimation of friction coefficients of a golf club head against different golf balls would facilitate designing of spin rate. The present invention provides a method of readily designing spin rate of a golf ball, wherein a collisional plate which is mounted in a detachable manner is created as a model of a golf club head, and a coefficient of dynamic friction is measured by bringing a golf ball into collision with the collisional plate, and then based on the measurement, a contact force and a coefficient of dynamic friction at the time of collision between an actual golf club head and the golf ball are estimated.

The present invention provides a method for measuring a coefficient of dynamic friction between a golf ball and a collisional plate when the golf ball collides with the collisional plate disposed aslant at a predetermined angle with respect to a flying direction of the golf ball. The method includes concurrently obtaining a time function $Fn(t)$ of contact force in the direction perpendicular to the collisional plate, and a time function $Ft(t)$ of contact force in the direction parallel with the collisional plate; and determining as a coefficient of dynamic friction, a maximum value of a time function $M(t)$ of ratio between $Fn(t)$ and $Ft(t)$ represented by $M(t)=Ft(t)/Fn(t)$.

The collisional plate is adjustable at an angle ($\alpha$) range of 10 degrees to 90 degrees with respect to the flying direction of the golf ball. Preferably, the collisional plate is mounted in a detachable manner. Further, the collisional plate may be attached with a pressure sensor.

In the measuring method of the present invention, the golf ball may be emitted vertically upward via an air gun system to collide with the collisional plate.

In the measuring method of the present invention, an initial velocity of the golf ball before collision with the collisional plate, and an angle of collisional plate may be controlled by a control box.

In the measuring method of the present invention, the collisional plate may include a substrate, a pressure sensor, a superficial plate, and a main bolt for integrally fixing them.

In the measuring method of the present invention, the substrate may be made of steel.

In the measuring method of the present invention, the superficial plate may include a main body and a covering plate, and a coefficient of dynamic friction may be measured while arbitrarily designing and varying a material, a planner shape and a surface structure of the covering plate.

In the measuring method of the present invention, the main body of the superficial plate may be made of stainless steel.

In the measuring method of the present invention, the covering plate of the superficial plate may be made of a titanium alloy containing 6% by mass of aluminum and 4% by mass of vanadium.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The measuring method of the present invention uses a detachably mounted collisional plate, and hence is a very close model for hit of an actual golf club. It can analyze collision phenomena such as contact force and a friction phenomenon at the time of collision between an actual golf club and a golf ball by measuring a coefficient of dynamic friction.

(Method of Measuring Coefficient of Dynamic Friction)

A method of measuring a coefficient of dynamic friction between a golf ball and a collisional plate in the present invention will be explained below with reference to a measuring apparatus of FIGS. 1 and 2.

Figure 1:
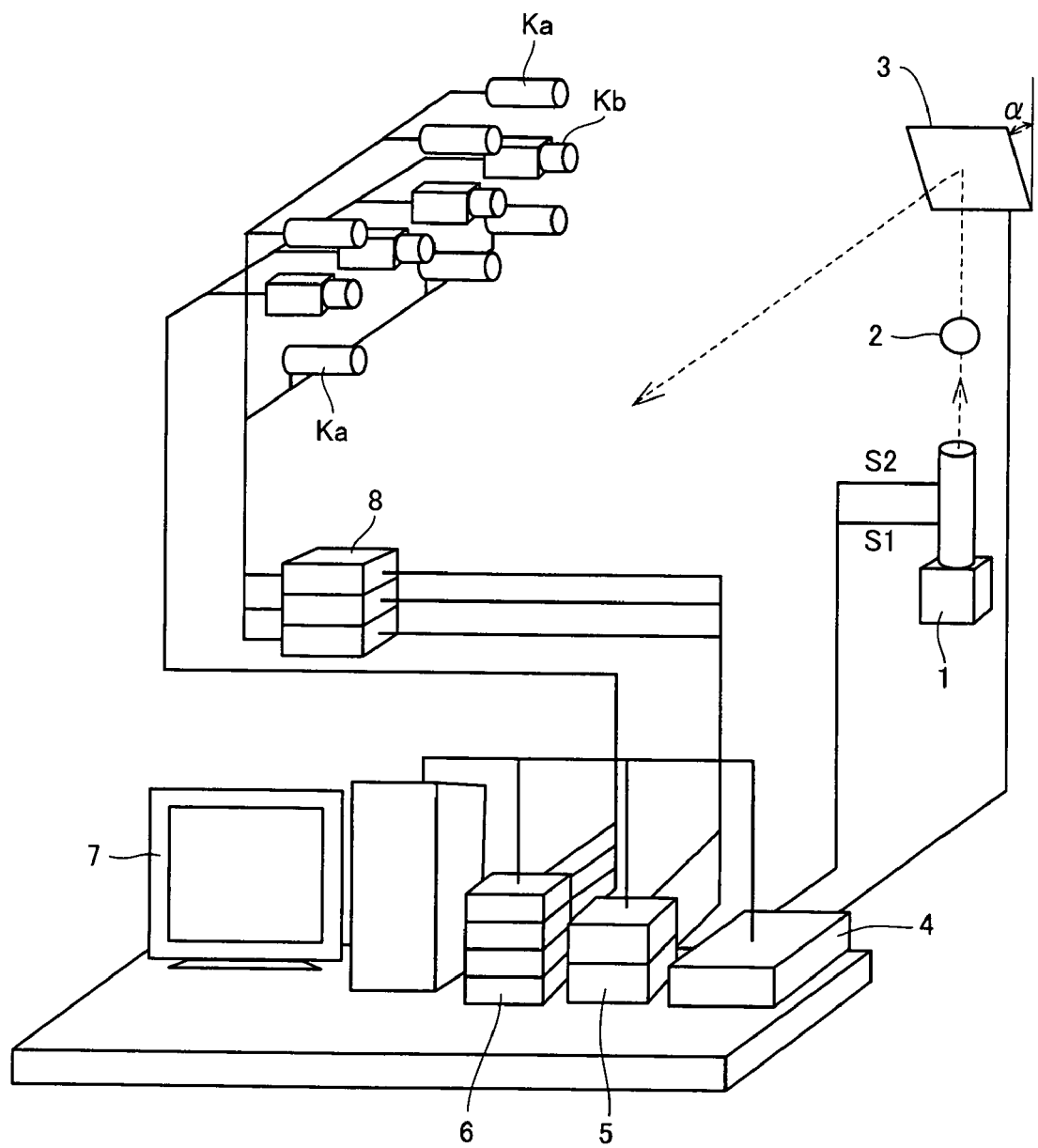
FIG. 1 is a schematic view of a measuring method used in the present invention.

In FIG. 1, a golf ball 2 is emitted upward perpendicularly in the vertical direction from an emitter 1 of an air gun system. Golf ball 2 is emitted at an initial velocity in the range of about 20 to 50 m/second, for example. The initial velocity of golf ball 2 is calculated by measuring a distance and a blocking time difference between a first sensor S1 and a second sensor S2.

Golf ball 2 thus emitted is brought into collision with a collisional plate 3 set in advance at a predetermined angle (α) in the emitting direction of golf ball (flying direction). These initial velocity of golf ball and angle (α) of collisional plate are controlled in a control box 4.

Golf ball 2 after collision is reflected in the left downward direction as shown in FIG. 1. Fn(t) which is time-series data of force along the direction perpendicular to the collisional plate and Ft(t) which is time-series data of force along the direction parallel with the collisional plate at the time of collision are measured by a pressure sensor 22 which is attached to collisional plate 3.

Figure 3:
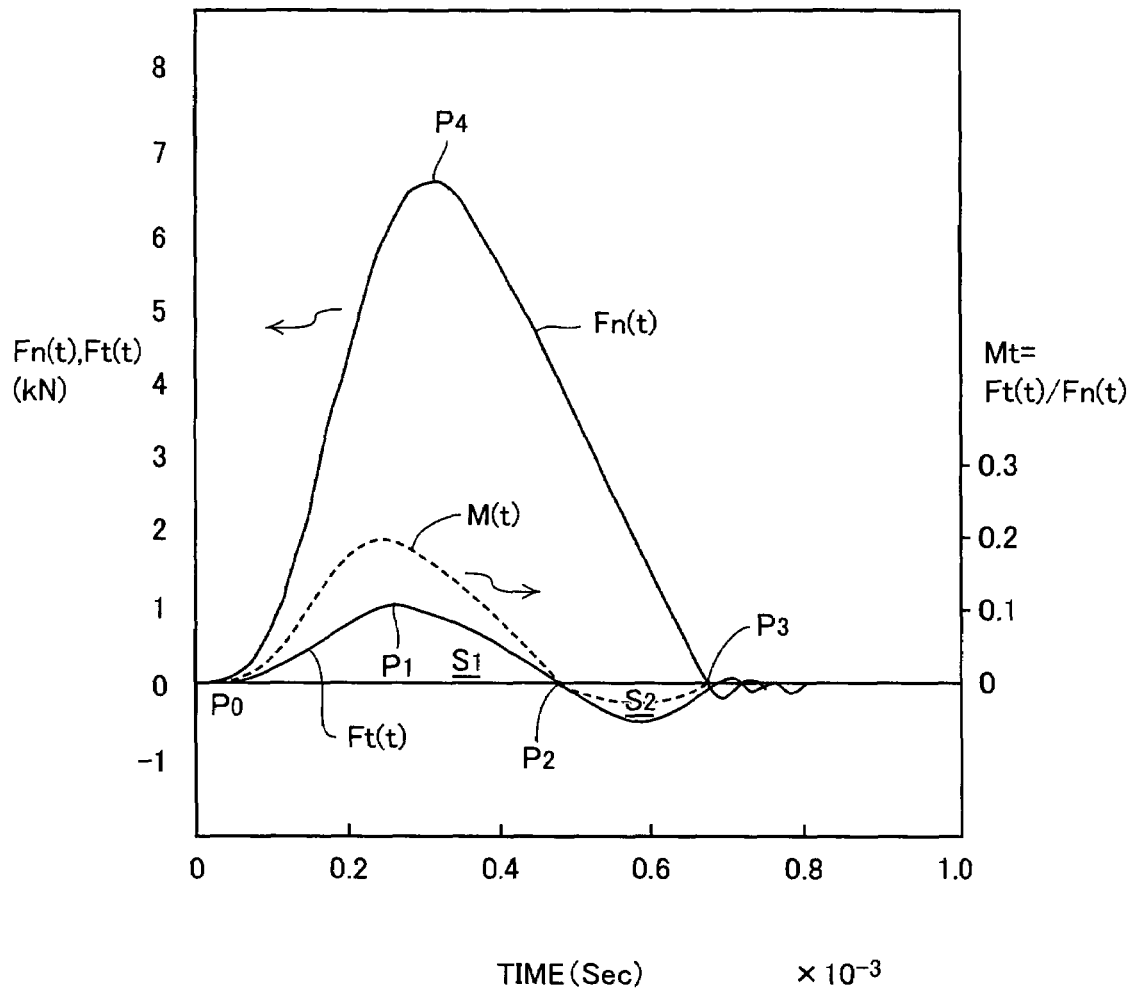
FIG. 3 is a graph showing $Ft(t)$, $Fn(t)$ and $M(t)$.

In FIG. 3, a point P0 represents a position where pressure sensor 22 starts sensing force, and generally corresponds to the point at which collisional plate 3 and golf ball 2 come into collision with each other. Fn(t) which is a contact force of perpendicular direction gradually increases from point P0, peaks at a point P4, comes down therefrom to reach zero at a point P3. Point P3 represents a point where pressure sensor 22 no longer senses force, and generally corresponds to the point where golf ball 2 leaves collisional plate 3.

On the other hand, a value of Ft(t) which is contact force in the direction parallel with the collisional plate (i.e., shear strength) increases with time from point P0, peaks at P1, then gradually decreases to zero at point P2 after which it takes a negative value. Since the golf ball leaves pressure sensor 22 at point P3, the curve of Ft(t) sensed at pressure sensor 22 takes zero at point P3. An area S1 of the region where Ft(t) takes positive values within the area surrounded by the curve of Ft(t) and the time axis represents impulse where shear strength is positive. On the other hand, an area S2 of the region where Ft(t) takes negative values within the area surrounded by the curve of Ft(t) and the time axis represents impulse where shear strength is negative. Impulse S1 acts in such a direction that promotes back spin, and impulse S2 acts in such a direction that restrains back spin. Here, impulse S1 takes a larger value than impulse S2, and a value obtained by subtracting impulse S2 from impulse S1 contributes to back spin of a golf ball.

A coefficient of dynamic friction can be derived by calculating a maximum value of M(t) which is obtainable by Ft(t)/Fn(t).

(Concurrent Measuring Method of Spin Rate of Golf Ball)

In the measuring apparatus of FIG. 1, spin rate, speed, and launch angle of a golf ball that collides with the collisional plate are measured. This may be used as identification data for determining correlation between calculated value of M(t) and spin rate.

In FIG. 1, golf ball 2 that is reflected by the collisional plate is measured for spin rate, speed and flying angle of golf ball 2 during fly by a stroboscopic device Kb and a camera device Ka disposed laterally of the flying trajectory. Stroboscopic device Kb is connected to a stroboscopic power 5, and camera device Ka is connected to a camera power 6 via a capacitor box 8. Spin rate, speed, and flying angle may be analyzed by using a spin analyzing device 7. Further, by comparing these analysis results with results of measured coefficient of dynamic friction, it is possible to evaluate correlation between coefficient of dynamic friction and spin rage, as well as influences of coefficient of dynamic friction on the initial velocity and flying angle of a golf ball.

(Structure of Collisional Plate)

Figure 2:
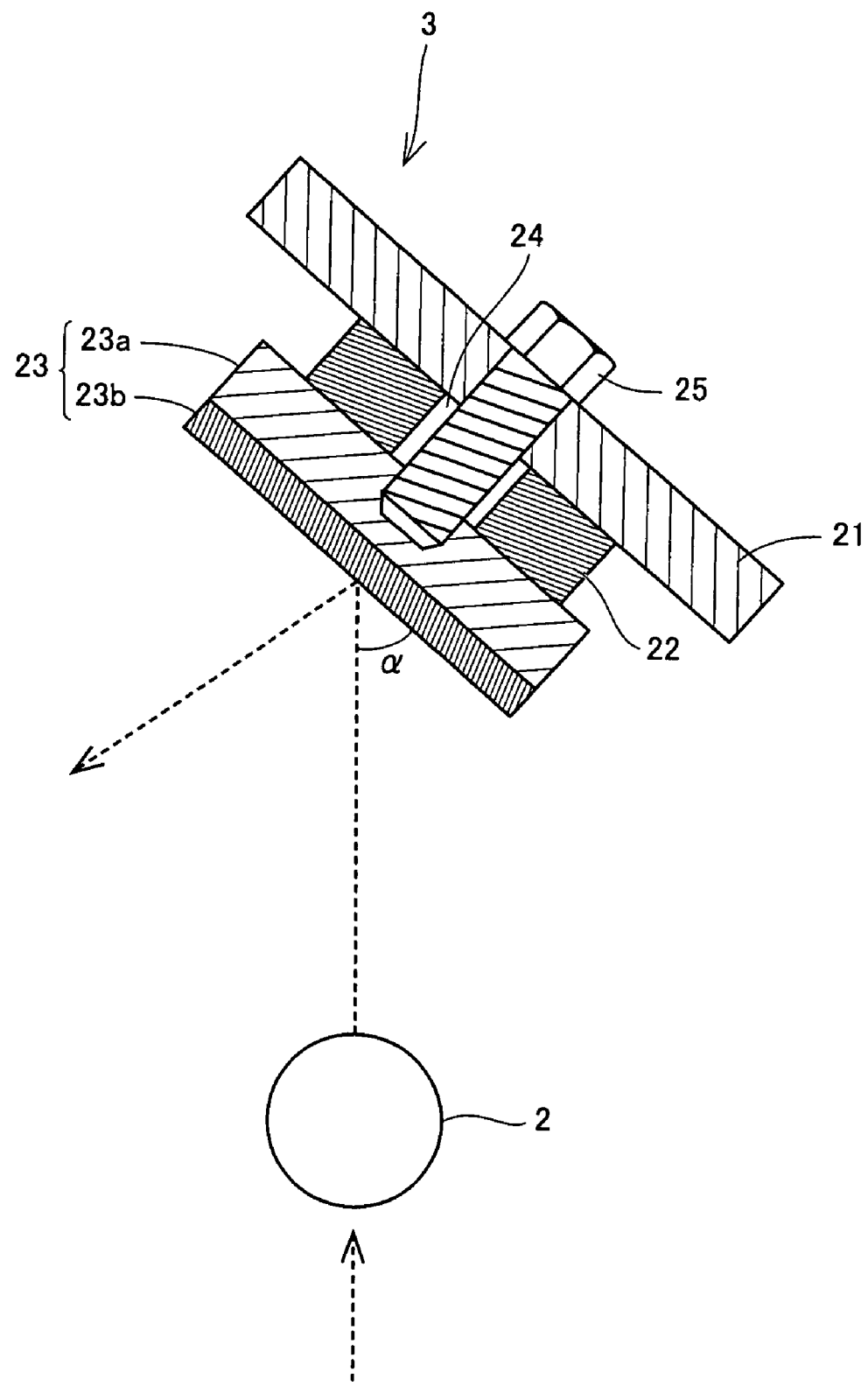
FIG. 2 is an enlarged partial section view of a collisional plate used in FIG. 1.

In FIG. 2, collisional plate 3 has a substrate 21, pressures sensor 22, a superficial plate 23 and a main bolt 25 for integrally fixing these elements.

Substrate 21 may be formed of any material without particular limitation insofar as it has a predetermined strength and rigidity, but preferably formed of steel. Substrate 21 is 5.0 to 20.0 mm thick. A model number of main bolt 25 is, for example, M10 according to Japanese Industrial Standards (JIS).

Pressure sensor 22 may be implemented by a variety of products such as 3-component force sensor (model 9067) manufactured by Kistler Instrument Corp., for example. This sensor is able to measure force components in a parallel direction, a Y direction and a perpendicular direction. Although not illustrated, measurement of pressure is conducted with a charge amplifier (model 5011B of Kistler Instrument Corp.) connected to pressure sensor 22. Pressure sensor 22 is formed in its center with a through-hole 24 through which main bolt 25 is inserted to integrally fix pressure sensor 22 with substrate 21.

Superficial plate 23 is made up of a main body 23a and a covering plate 23b. The covering plate is attached to the main body in a detachable manner. By appropriately changing the material, the planner shape and the surface structure of covering plate, it is possible to create approximate models of various golf club heads and to measure coefficients of dynamic friction thereof. Main body 23a and covering plate 23b may be mounted in any way without special limitation, for example, via a bolt.

Main body 23a of superficial plate 23 may be formed of any materials without limitation, but typically of stainless steel (SUS-630). The thickness of main body 23a is typically in the range of 10 to 20 mm. Also, main body 23a may have a planner shape which is substantially the same with that of pressure sensor 22, such as a square 40-60 mm on a side. Into main body 23a, a distal end of main bolt 25 is screwed. As a result, pressure sensor 22 is sandwiched and fixedly positioned between substrate 21 and main body 23a.

As to covering plate 23b, various materials, planner shapes and surface structures may be adopted, however, a titanium alloy (6-4Ti) containing 6 wt % of aluminum and 4 wt % of vanadium is typically used in view of evaluation of model of club head. Thickness of covering plate 23b may be arbitrarily changed, for example, within the range of 1.0 to 5.0 mm. The planner shape of covering plate 23b is substantially the same with that of main body 23a, such as a square 40-60 mm on a side, for example. Also, covering plate 23b has a surface roughness which may be arbitrarily adjusted, for example in the range of 2 to 20 μm in terms of 10-point average roughness Rz.

Collisional plate 3 may be positioned at any angle (α) with respect to the flying direction (launching direction) of golf ball. In the present invention, the angle (α) is typically adjusted in the range of 10° to 90°. This angle corresponds to a loft angle of golf club and may be efficiently used for designing different numbers of club heads.

EXAMPLES

A coefficient of dynamic friction of a golf ball was measured using a measuring apparatus having a general structure shown in FIG. 1 and having the following specification.

1. Specification of Measuring Apparatus
    (A) Emitter: air gun system
    (B) Collisional plate Substrate
    Steel
    Thickness: 5.35 mm Main body
    Superficial plate
    Size: 56 mm×56 mm×15 mm
    Stainless steel (SUS-630)
    Covering plate
    Size: 56 mm×56 mm×2.5 mm
    Titanium alloy: 6-4Ti (6 wt % Al, 4 wt % V)
    Average roughness: 13.6 μm±2.0 μm
    Angle of inclination ($\alpha$)
    22 degrees (with respect to flying direction of golf ball)
    (C) Pressure sensor
    3-component force sensor (model 9067), product of Kistler Instrument Corp.

Charge amplifier
    Model 5011B, product of Kistler Instrument Corp.
    (D) Capture of contact force into PC
    A pulse counter board PCI-6101 (manufactured by INTERFACE CORPORATION) was used. With a 16-bit PCI pulse counter board with 4 channels, measurement suited for a specific application may be realized in four counter modes. The maximum input frequency is 1 MHz.

2. Measuring Procedure
    Measurement of coefficient of dynamic friction was conducted in the following manner.
    (a) Set angle (a) of collisional plate at 22 degrees with respect to flying direction of golf ball (vertical direction).
    (b) Adjust air pressure of emitter 1.
    (c) Emit golf ball from emitter.
    (d) Measure initial velocity of golf ball from preset distance between sensor 1 and sensor 2 and blocking time difference of golf ball therebetween.
    (e) Measure contact force Fn(t) and contact force Ft(t), and calculate maximum value of Ft(t)/Fn(t).
    (f) Measure spin rate of golf ball with stroboscopic device and camera device.

3. Result of Measurement
    Results obtained with the above apparatus and measuring procedure are shown in FIG. 3. From FIG. 3, a value of M(t) is calculated as Ft(t)/Fn(t), and a maximum value is 0.21. Since Ft and Fn tend to generate noises in initial and terminal periods where contact force rises up, a maximum value of M(t) is calculated while trimming an early stage of the initial period and a late stage of the terminal period.

The present invention provides a method capable of adjusting a contact force between a golf ball and a golf club, and a spin rate of the golf ball when the golf ball is hit by the golf club. The present invention allows for evaluation of spin rate at the time of hitting with a golf club by measuring a coefficient of dynamic friction between a golf ball and a collisional plate in an apparatus employing a club model with the collisional plate.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A method for measuring a coefficient of dynamic friction between a golf ball and a collisional plate when the golf ball collides with the collisional plate disposed aslant at a predetermined angle with respect to a flying direction of the golf ball, the method comprising the steps of:
    concurrently obtaining a time function Fn(t) of a contact force in a direction perpendicular to the collisional plate, and a time function Ft(t) of a contact force in a direction parallel with the collisional plate; and
    determining as a coefficient of dynamic friction, a maximum value of a time function M(t) of a ratio between Fn(t) and Ft(t) represented by M(t)=Ft(t)/Fn(t).

2. The measuring method according to claim 1, wherein the collisional plate is adjustable at an angle range of 10 degrees to 90 degrees with respect to the flying direction of the golf ball.

3. The measuring method according to claim 1, further comprising the step of mounting the collisional plate in a detachable manner.

4. The measuring method according to claim 1, further comprising the step of attaching the collisional plate with a pressure sensor.

5. The measuring method according to claim 1, further comprising the step of emitting the golf ball vertically upward via an air gun system to collide with the collisional plate.

6. The measuring method according to claim 1, wherein an initial velocity of the golf ball before collision with the collisional plate, and an angle of collisional plate are controlled by a control box.

7. The measuring method according to claim 1, wherein the collisional plate comprises a substrate, a pressure sensor, a superficial plate, and a main bolt for integrally fixing the substrate, the pressure sensor and the superficial plate together.

8. The measuring method according to claim 7, wherein the substrate comprises steel.

9. The measuring method according to claim 7, wherein the superficial plate comprises a main body and a covering plate, said method further comprising the step of measuring a coefficient of dynamic friction while arbitrarily designing and varying a material, a planar shape and a surface structure of the covering plate.

10. The measuring method according to claim 7, wherein the main body of the superficial plate comprises stainless steel.

11. The measuring method according to claim 7, wherein the covering plate of the superficial plate comprises a titanium alloy containing 6 wt % of aluminum and 4 wt % of vanadium.

\* \* \* \* \*